United States Patent [19]

Johnson et al.

[11] Patent Number: 4,540,664
[45] Date of Patent: Sep. 10, 1985

[54] METHOD OF SACCHARIFYING CELLULOSE

[75] Inventors: Eric A. Johnson, Brookline; Arnold L. Demain, Wellesley, both of Mass.; Ashwin Madia, Decatur, Ill.

[73] Assignee: The United States of America as represented by the United States Department of Energy, Washington, D.C.

[21] Appl. No.: 494,482

[22] Filed: May 13, 1983

[51] Int. Cl.³ .......................... C12P 19/14; C12N 1/22; C12R 1/145
[52] U.S. Cl. ..................................... 435/99; 435/252; 435/842
[58] Field of Search ................. 435/99, 163, 165, 209, 435/252

[56] References Cited

U.S. PATENT DOCUMENTS 4,443,542 4/1984 Hayashida et al. ................. 435/160

OTHER PUBLICATIONS

Eur. J. Appl. Microbiol. Biotechnol., 9:190–197, (1980).
Anal. Biochem., 72:248–254, (1976).
Can. J. Microbiol., 27:517–530, (1981).
Biochem. J., 95:270–281, (1965).
Biochem. J., 100:315–320, (1966).
J. Gen. Microbiol., 32:441–448, (1963).
Biochem. J., 135:587–594, (1973).
J. Gen. Microbiol., 126:211–217, (1981).
Anal. Biochem., 73:369–377, (1976).
J. Gen. Microbiol., 121:499–502, (1980).
Biotechnol., Bioeng. Symp., 6:21–33, (1976).
Bacteriol., Rev., 14: 51–63, (1950).
Arch. Microbiol., 114:1–7, (1977).
Appl. Environ. Microbiol., 42:231–240, (1981).
Enzyme Microbiol. Technol., 2:91–102, (1980).
Appl. Environ. Microbiol., 33:289–297, (1977).

Primary Examiner—Lionel M. Shapiro
Attorney, Agent, or Firm—James W. Weinberger; Walter L. Rees; Judson R. Hightower

[57] ABSTRACT

A method of saccharifying cellulose by incubation with the cellulase of Clostridium thermocellum in a broth containing an efficacious amount of a reducing agent. Other incubation parameters which may be advantageously controlled to stimulate saccharification include the concentration of alkaline earth salts, pH, temperature, and duration. By the method of the invention, even native crystalline cellulose such as that found in cotton may be completely saccharified.

16 Claims, 5 Drawing Figures

4,540,664

METHOD OF SACCHARIFYING CELLULOSE

CONTRACTUAL ORIGIN OF THE INVENTION

The United States Government has rights in this invention pursuant to Contract No. EG-77-C-02-4198 between the U.S. Department of Energy and the Midwest Research Institute through its Solar Energy Research Institute Division and Subcontract XR-9-8109-1 thereunder with the Massachusetts Institute of Technology.

BACKGROUND OF THE INVENTION

This invention relates to a method of saccharifying cellulose by use of the cellulase of *Clostridium thermocellum*. More particularly, this invention relates to a method of saccharifying cellulose by use of the cellulase of *Clostridium thermocellum* wherein the saccharification is enhanced by the presence of thiol reducing agents and also by the presence of $Ca^{2+}$.

There has been great interest in recent years in microbial processing of cellulosic material to provide new sources of energy, chemicals, and single-cell protein. In particular, much effort has been devoted to the conversion of native forms of cellulose to valuable fermentation products such as ethanol. The rate-limiting step in this process is the depolymerization of cellulose to sugars, known as saccharification. This limitation is imposed to various extents by the proportion of cellulose which is in the crystalline state as opposed to the amorphous state. Native cotton, for example, has a very high proportion of crystalline cellulose and is therefore difficult to saccharify.

It is known that a true cellulase will saccharify even native cotton. Such cellulases are secreted by certain fungi and bacteria. The cellulase of the fungus *Trichoderma reesei* has been found to have a particularly high saccharification activity. Significantly, the activity is retained in cell-free filtrates containing the cellulase. The cellulase of *T. reesei* is therefore used as an industry standard in measuring relative saccharification.

The anaerobic, thermophilic bacterium *Clostridium thermocellum* has heretofore been believed to have only limited saccharification activity. The extracellular fluid of this species contains carboxymethyl-cellulase, an enzyme reported to have weak activity which is oxygen-stable and unaffected by $Ca^{2+}$ with respect to saccharification of crystalline cellulose. Generally, the extracellular bacterial cellulases do not exhibit the extensive saccharification of crystalline cellulose characteristic of the extracellular fungal cellulases. However, as the bacteria may grow more rapidly than the fungi on either amorphous or crystalline cellulose, it would be desirable to increase the saccharification activity of the extracellular bacterial cellulases, and in particular the cellulase of *C. thermocellum*.

SUMMARY OF THE INVENTION

It is thus one object of the invention to provide a method of saccharifying cellulose with the extracellular cellulase of *Clostridim thermocellum*.

It is another object of the invention to provide a method of saccharifying cellulose with the extracellular cellulase of *Clostridium thermocellum* wherein the saccharification is stimulated by the presence of reducing agents and $Ca^{2+}$.

Additional objects, advantages, and novel features of the invention will be set forth in part in the following description.

In accordance with the invention, a method is disclosed for saccharifying cellulose comprising incubating the cellulose in an incubation mixture containing extracellular cellulase from *Clostridium thermocellum* and also a quantity of a reducing agent sufficient to allow saccharification. In particular, thiol reducing agents are effective for this purpose. The reducing agent is present in low concentrations, preferably at least 0.5 millimolar (mM) and generally less than 10 mM. A preferred thiol reducing agent is dithiothreitol. The saccharification is further stimulated by the presence of alkaline earth salts. The ion $Ca^{2+}$ is especially efficacious in this regard. Preferably, the incubation mixture is at a pH between about 4.5 to about 9.0, is at a temperature between about 40° C. and about 75° C., and is incubated for a duration of about 20 hours to about 160 hours.

Incubation under these conditions will almost completely saccharify even crystalline cellulose such as native cotton. The instant invention thus provides a method by which the extracellular cellulase of the bacterium *C. thermocellum* saccharifies native and derived forms of cellulose at a rate and to an extent comparable with *T. reesei*.

DETAILED DESCRIPTION OF THE PREFERRED EMBODIMENT

Figure 1:
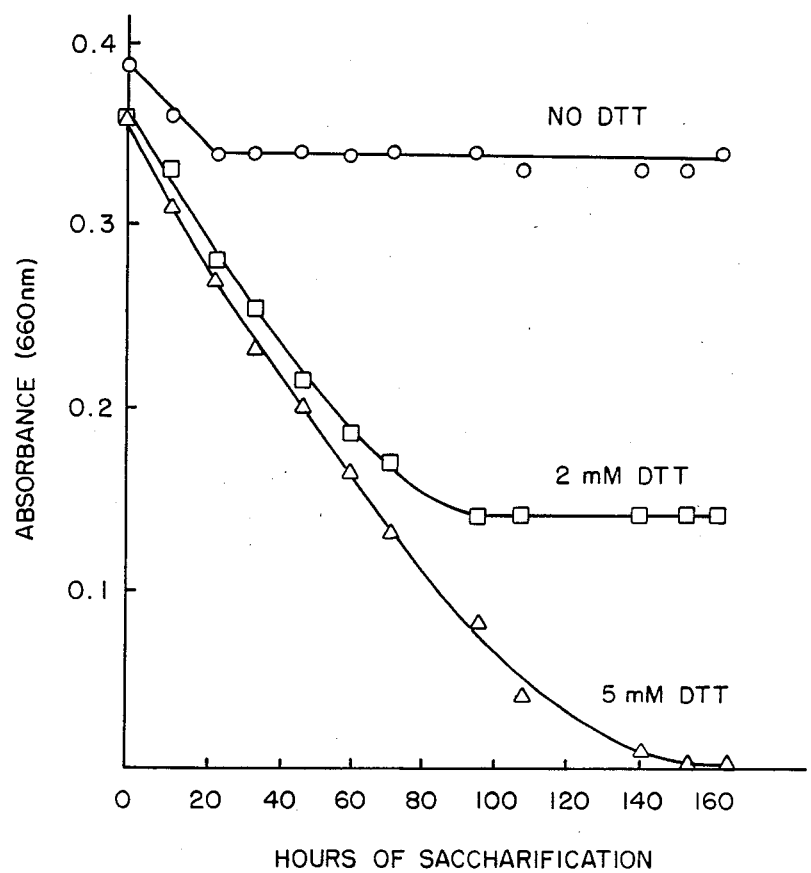
FIG. 1 illustrates the effect of dithiothreitol concentration on cellulose saccharification by measuring as a function of time the absorbance of incubation mixtures containing different amounts of dithiothreitol.

The following is a detailed description of a preferred embodiment. Other embodiments will be readily apparent to those skilled in the art.

The instant invention is a method of saccharifying cellulose wherein the cellulose is incubated in an incubation mixture containing extra-cellular cellulase of *C. thermocellum* in the presence of a reducing agent. The reducing agent may be a thiol reducing agent, preferably dithiothreitol. The saccharification is stimulated by the presence of an alkaline earth salt, preferably one containing $Ca^{2+}$.

The particular embodiments of the method of the invention and the results it gives as described herein are more readily understood if one first understands the sources of the cellulase used. Therefore, the particular sources of the *C. thermocellum* cellulase used to test the invention will be described; it is understood that the method of the instant invention is not limited to the particular sources of *C. thermocellum* cellulase described herein and that other sources of the cellulase may be used and are contemplated as being within the scope of the appended claims.

A first batch of cellulase was prepared by growing *C. thermocellum* ATTC 27405 in a fermentor on modified CM-3 cellobiose medium at 60° C. and 60 rpm for 68 hours. Modified CM-3 cellobiose is a liquid growth medium containing yeast extract, mineral salts and crysteine, described by Garcia-Martinez et al. in *Eur. J. Appl. Microbiol. Biotechnol,* 9:187-197, 1980. Cysteine is a reducing agent known to promote bacterial growth. The resulting liquid, known as a broth, was chilled to 4° C. and then centrifuged at 18,000×g for 20 minutes to remove cells. The supernatant fluid, which comprised the cell-free broth, was purified as follows: The supernatant fluid was treated with solid $(NH_4)_2SO_4$ to 80% saturation and stored overnight at 4° C. The precipitate was harvested by centrifugation, dissolved in 50 mM sodium citrate buffer (pH 5.7), reprecipitated by addition of 4 volumes of saturated $(NH_4)_2SO_4$ and again stored overnight before dissolution in the citrate buffer. The preparation was desalted by passage through the gel filtration resin Biogel P-2 (Bio-Rad Laboratories, Richmond, CA) diluted to 1 mg protein $ml^{-1}$, and stored frozen.

A second batch of cellulase was prepared by growing the same strain of *C. thermocellum* in a larger fermentor containing 0.5% Solka Floc SW-40 (Brown Co., Berlin, NH), a type of purified non-crystalline cellulose which served as a carbon source. The liquid was stirred at 50 rpm and gassed with $N_2$ for the first 19 hours of the 60 hour fermentation. At 60 hours, cysteine.HCl was added to a final concentration of 0.1% and the cells were removed by centrifugation. The resulting cell-free broth retained its saccharification activity for at least a month at 4° C., and for at least 4 months at −20° C. When required for enzymic work, it was centrifuged at 18,000×g for 15 minutes at room temperature and the supernatant fluid, containing about 0.2 mg protein $ml^{-1}$, was either used as such, or precipitated with $(NH_4)_2SO_4$ and the precipitate collected and redissolved in either acetic or succinate buffer.

By the method of the instant invention, incubation mixtures comprising cellulase-containing broths of *C. thermocellum,* of which the two broths described above are typical, are used to saccharify various types of cellulose. The method is particularly effective on native celluloses such as nonabsorbent cotton, which has a high degree of crystallinity. It is also effective on Avicel (type PH-105, 20 μm particles; FMC Corp., Marcus Hook, PA), which is a derived form of crystalline cellulose, and on cellulose which is largely non-crystalline such as common filter paper. The method also has some effect on carboxymethylcellulose (CM-cellulose), a derived non-crystalline cellulose. Activities will be described herein in terms of these cellulose-containing substrates.

The cellulose to be saccharified is incubated in a *C. thermocellum* cellulase-containing incubation mixture in the presence of a reducing agent. The benefits of using thiol reducing agents are unexpected, for while it was heretofore known that such reducing agents enhanced bacterial growth, it was not known that they would also promote saccharification when used with the extracellular cellulase. One of the most effective reducing agents for this purpose is dithiothreitol. The thiol reducing agents cysteine, glutathione, and mercaptoethanol are also known to be effective, as is sodium dithionite.

FIG. 1 illustrates the effect of different concentrations of dithiothreitol on the saccharification of Avicel. In these experiments 50 μg of the protein that had been desalted by passage through the gel filtration resin was incubated with 3 mg of the substrate in 3 ml of substrate buffer. The buffer was 0.1M succinic acid/NaOH with a pH of 5.5. The suspension was diluted to 5 ml. No $Ca^{2+}$ was added. The cellulase activity was monitored by the decrease in turbidity of the suspension measured at 660 nm. By this method, the turbidity of the suspension decreases as more cellulose is saccharified, and less light is absorbed. The pronounced effect of the dithiothreitol (DTT) on the extent of saccharification is evident from the Figure. When no reducing agent is added, saccharification ceases after about 20 hours. When the suspension is 2 mM in DTT the saccharification continues over 90 hours and is much more extensive, and when the suspension is 5 mM in DTT the rate of saccharification is greater and the saccharification continues for about 160 hours until all the cellulose has been consumed. It is seen that the presence of the thiol reducing agent greatly increases the saccharification activity of the incubation mixture. This effect has been noted at DTT concentrations as low as 1 mM. The effect is especially pronounced in the incubation mixture containing the broth treated with the gel filtration resin, which treatment also removes cysteine, a thiol reducing compound, from the growth medium. However, the same stimulatory effect was observed to a lesser extent with unpurified extracellular broth and with the $(NH_4)_2SO_4$ precipitated cellulase that had not been desalted.

Figure 2:
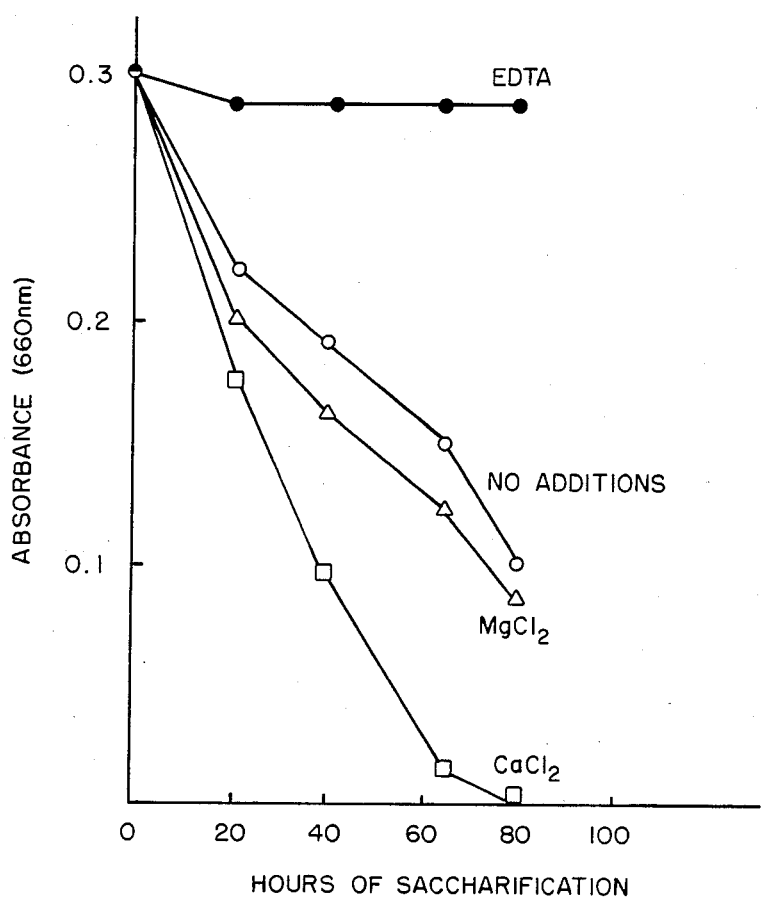
FIG. 2 illustrates the effect of alkaline earth salts on cellulose saccharification by measuring as a function of time the absorbance of incubation mixtures containing a chelating agent, no additions, $MgCl_2$ and $CaCl_2$.

The saccharification activity of the *C. thermocellum* cellulase is also stimulated by alkaline earth salts, particularly $Ca^{2+}$. FIG. 2 illustrates this effect. The reaction conditions were the same as for the samples used in FIG. 1 except that each sample included 5 mM DTT and either no additions, 10 mM EDTA, 7 mM $CaCl_2$, or 7 mM $MgCl_2$. EDTA, a chelating agent which forms complexes with any alkaline earth cations which may already be present in the reaction mixture, completely inhibits saccharification. Addition of $MgCl_2$ slightly improves the extent of saccharification when compared with the sample to which no salts were added. $CaCl_2$ is much more effective, enabling the cellulase to achieve complete saccharification of the substrate in only half the time required when no salt is added. Salt concentrations may range from about 1 mM to about 10 mM or greater.

Figure 3:
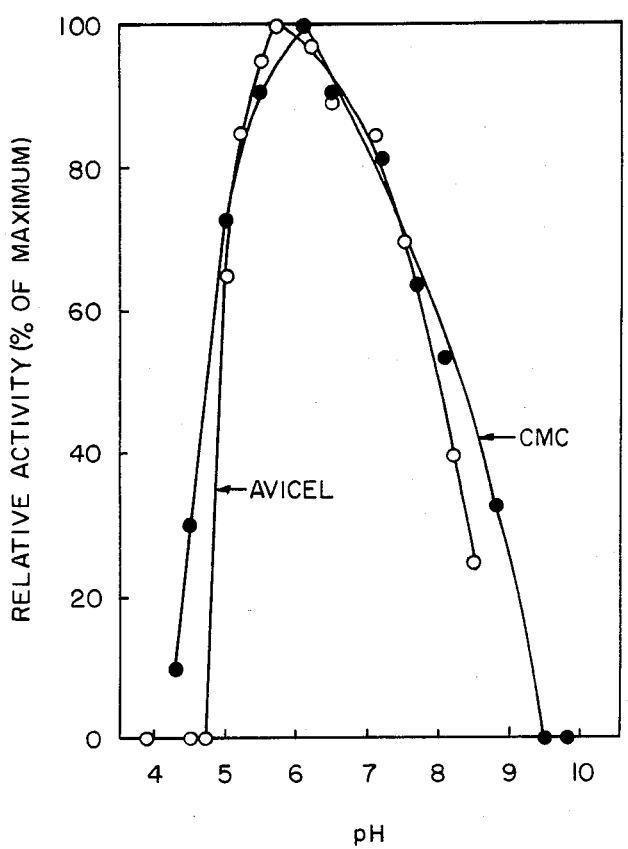
FIG. 3 illustrates the effect of pH on the activity of *C. thermocellum* cellulase on different forms of cellulose.

Saccharification by the method of the instant invention is also stimulated by the proper pH. FIG. 3 summarizes the results of a series of experiments on the activity of *C. thermocellum* cellulase on Avicel and on carboxymethyl cellulose at different pH levels. The activities were measured with the ammonium sulfate precipitated cellulase in an incubation mixture containing 10 mM DTT and 7 mM $Ca^{2+}$. Relative activities were greatest at a pH of about 6.1 for non-crystalline CM-cellulose and about 5.7 for crystalline Avicel. The cellulase preparation showed similar behavior in both acetate and succinate buffer between pH 4.0 and 6.5.

Figure 4:
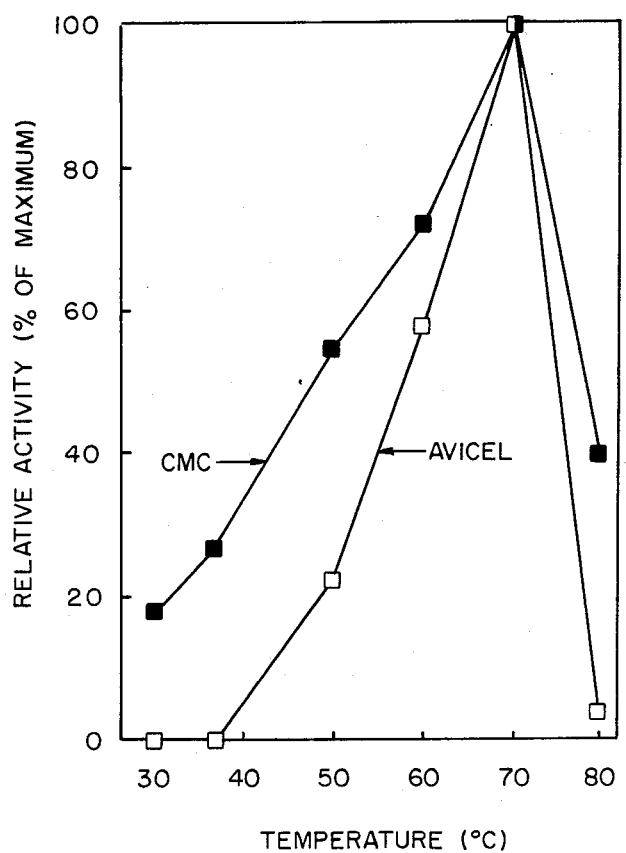
FIG. 4 illustrates the effect of temperature on the activity of *C. thermocellum* cellulase on different forms of cellulose.

Temperature is another parameter which can be modified to enhance the method of the instant invention. FIG. 4 illustrates the effect of temperature on the saccharification activity of the ammonium sulfate precipitated cellulase on CM-cellulose and Avicel. The activities on both substrates was at a maximum at 70° C. At 80° C., the activity on Avicel was almost nonexistent while the preparation retained 40% of its potency toward CM-cellulose.

Temperature also affects the stability of the extracellular cellulase. Table I shows the results of a series of experiments in which substrate-free samples of the cellulase were maintained at pre-selected temperatures at a pH of 5.8 for 5 hours, and then incubated with Avicel for 16 hours at 60° C. The cellulase lost all activity in 5 hours at 80° C. but lost only 15% of its activity between 37° and 70° C. Results were measured turbidimetrically. In another series of experiments, substrate-free samples of the cellulase were maintained at the same pre-selected temperatures and pH but for only 45 minutes. As shown in Table I, these samples showed marked loss in activity toward CM-cellulose even at 30° C., followed by increasing losses up to 80° C. These results suggest the presence of more than one enzymatic component in the extracellular cellulase of C. thermocellum.

TABLE I

| Temp (°C.) | Residual activity (%) | |
|---|---|---|
| | To CM-cellulose | To Avicel |
| 30 | 31 | 85 |
| 37 | 56 | 85 |
| 50 | 38 | 85 |
| 60 | 25 | 85 |
| 70 | 13 | 85 |
| 80 | 13 | 0 |

Figure 5:
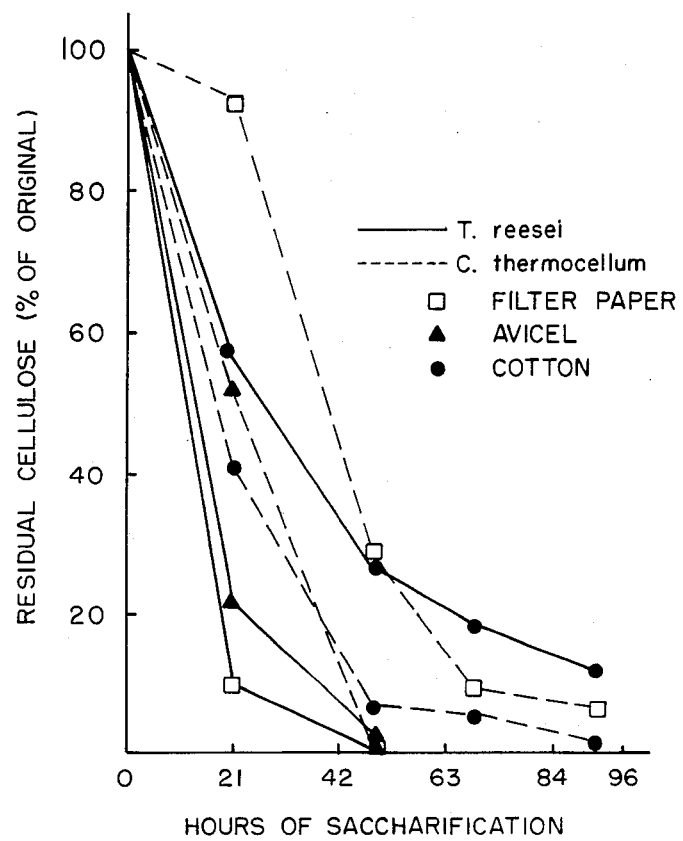
FIG. 5 illustrates the extent of saccharification of various native and derived forms of cellulose by the cellulases of *T. reesei* and *C. thermocellum*.

The C. thermocellum cellulase, under proper conditions, saccharifies not only the micro-crystalline Avicel but native cotton and filter paper as well. It thus acts as a true cellulase. FIG. 5 compares the saccharification activity of the cellulases of C. thermocellum and T. reesei (the industry standard) on cotton, Avicel, and filter paper. In these experiments equal broth volumes of the extracellular broth from C. thermocellum grown on Solka-Floc (0.2 mg protein ml$^{-1}$) and T. reesei QM9414 (9.5 mg protein ml$^{-1}$) cellulase were used. The samples with T. reesie cellulase were incubated at 37° C. in a 0.2M sodium acetate/acetic acid buffer of pH 4.8. The samples with C. thermocellum cellulase were incubated at 60° C. in the pH 5.5 succinate buffer and contained 7 mM CaCl$_2$ and 10 mM DTT. Saccharification was measured by loss in weight of the substrate and also, for the T. reesei cellulase samples, as a function of the total soluble carbohydrate in the suspension and as a function of glucose and cellobiose in the suspension. These latter methods gave results similar to those obtained from loss in weight, indicating that the products were essentially all glucose. As the Figure indicates, under the reaction conditions of the instant invention, the C. thermocellum cellulase reacts most rapidly in the early stages with native cotton while filter paper is the most resistant to saccharification. T. ressei cellulase shows the opposite pattern, saccharifying filter paper the most readily while being much less reactive toward cotton. It is especially noteworthy that when C. thermocellum cellulase is used in accordance with the method of the instant invention it can achieve saccharification which is at least equal to that of the industry standard and at a much lower protein concentration.

A further set of experiments compared the saccharification properties of C. thermocellum cellulase at its optimum temperature of 60° C. with the saccharification properties of T. reesei cellulase at 37° C. and 50° C. These two temperatures are known to be optimum saccharification temperatures for two components of the T. reesei cellulase. Under these conditions, the cellulase of C. thermocellum was more effective than the cellulase of T. reesei for both Avicel and native cotton.

The foregoing description of a preferred embodiment is not intended to limit the invention to the precise form disclosed. Obviously many modifications and variations are possible in view of the above disclosure. For example, scaling up of the inventive method to industrial levels may involve variations of the incubation parameters. The embodiments herein were chosen and described in order to best explain the principles of the invention and its practical application.

The embodiments of this invention in which an exclusive property or privilege is claimed are defined as follows:

1. A method of saccharifying cellulose comprising: incubating said cellulose in an incubation mixture with a substantially cell-free cellulase-containing broth from Clostridium thermocellum and a quantity of a reducing agent sufficient to allow saccharification.

2. The method of claim 1 wherein the reducing agent is a thiol reducing agent.

3. The method of claim 2 wherein the thiol reducing agent is selected from the group consisting of dithiothreitol, cysteine, glutathione, and mercaptoethanol.

4. The method of claim 1 wherein the reducing agent is sodium dithionite.

5. The method of claim 3 wherein said thiol reducing agent is dithiothreitol, being present in a concentration of at least 1.0 mM.

6. The method of claim 5 wherein said dithiothreitol is present in a concentration of about 2 mM to about 10 mM.

7. The method of claim 1 wherein said incubation mixture further contains a quantity of an alkaline earth salt sufficient to stimulate saccharification.

8. The method of claim 7 wherein said alkaline earth salt is a salt of calcium or magnesium.

9. The method of claim 8 wherein said alkaline earth salt is CaCl$_2$.

10. The method of claim 9 wherein said CaCl$_2$ is present in a concentration of at least 1 mM.

11. The method of claim 9 wherein said CaCl$_2$ is present in a concentration of at least 7 mM.

12. The method of claim 1 wherein the pH of said incubation mixtures is in the range of about 4.5 to about 9.

13. The method of claim 12 wherein the pH of said incubation mixture is in the range of about 5.0 to about 6.5.

14. The method of claim 1 wherein the temperature of said broth is maintained between about 40° C. and about 75° C.

15. The method of claim 14 wherein the temperature of said broth is maintained between about 65° C. and about 70° C.

16. The method of claim 1 wherein said incubation is of a duration of about 20 hours to about 160 hours.

* * * * *